United States Patent [19]

Jenkins et al.

[11] Patent Number: 5,304,699
[45] Date of Patent: Apr. 19, 1994

[54] PROCESS FOR THE REMOVAL OF GREEN OIL FROM A HYDROCARBON STREAM

[75] Inventors: Christopher D. W. Jenkins, Elwood, Australia; Michel H. Masson, Lillebonne, France; Richard A. Reitz, Houston, Tex.

[73] Assignee: Exxon Chemical Patents Inc., Linden, N.J.

[21] Appl. No.: 49,242

[22] Filed: Apr. 19, 1993

Related U.S. Application Data

[63] Continuation of Ser. No. 812,507, Dec. 20, 1991, abandoned.

[51] Int. Cl.$^5$ .................................. C07C 7/08
[52] U.S. Cl. ........................... 585/810; 585/601; 585/833; 585/860; 585/864; 203/57
[58] Field of Search ........... 585/601, 810, 833, 860, 585/864; 203/57

[56] References Cited

U.S. PATENT DOCUMENTS

| | | | |
|---|---|---|---|
| 2,377,847 | 6/1945 | Allen et al. | 585/615 |
| 4,101,451 | 7/1978 | Frevel et al. | 502/315 |
| 4,237,330 | 12/1980 | Lindner et al. | 585/810 |
| 4,316,796 | 2/1982 | Atlani et al. | 585/810 |
| 4,401,515 | 8/1983 | Arakawa et al. | 585/864 |
| 4,515,661 | 5/1985 | Ogura et al. | 585/860 |
| 4,647,344 | 3/1987 | Lindner et al. | 585/810 |
| 4,859,286 | 8/1989 | Kaibel et al. | 585/864 |

FOREIGN PATENT DOCUMENTS 0892470 3/1962 United Kingdom .

OTHER PUBLICATIONS

Kirk-Othmer, "Encyclopedia of Chemical Technology," Third Ed. vol. 4, 1978, pp. 356, 357.

Primary Examiner—Anthony McFarlane
Attorney, Agent, or Firm—L. K. Russell

[57] ABSTRACT

Disclosed is a process for removing hydrogenation by-products which comprises the use of an extractive distillation tower operated in combination with a solvent stripper, hydrocarbon purge and a water wash column. By the arrangement of the various feeds to and between the above mentioned, the green oil may be extracted away from desirable hydrocarbons.

22 Claims, 2 Drawing Sheets

PROCESS FOR THE REMOVAL OF GREEN OIL FROM A HYDROCARBON STREAM

This is a continuation of application Ser. No. 07/812,507, filed Dec. 20, 1991, now abandoned.

BACKGROUND OF THE INVENTION

1. Field Of The Invention

This invention relates to processes for hydrocarbon processing. In another aspect, this invention relates to processes for the removal of contaminants from hydrocarbons. In still another aspect, this invention relates to processes for the removal of butadiene derivative contaminants from a cracked hydrocarbon stream.

2. Description Of The Prior Art

Cracking is a well known process involving decomposition and molecular recombination of organic compounds, especially hydrocarbons obtained by means of heat to form molecules suitable for motor fuels, monomers, petrochemicals, etc. A series of condensation reactions takes place accompanied by transfer of hydrogen atoms between molecules which brings about fundamental changes in their structure. Methods of hydrocarbon cracking include thermal cracking, which utilizes heat to carry out the cracking, and catalytic cracking, which utilizes a catalyst generally either with the moving-bed or fluid-bed technique.

Steam cracking is widely used for the production of light olefins from saturated hydrocarbons. Reaction conditions for steam cracking of saturated hydrocarbons are selected to maximize the production of light olefins. Typically, cracking is practiced at a weight ratio of 0.3:1.0 of steam to hydrocarbon with the reactor coil outlet at 760°–870° C., and slightly above 100 kPa (atmospheric) pressure.

The type of feedstocks and the reaction conditions determine the mix of hydrocarbon products produced. Many steam crackers operate on light paraffin feeds consisting of ethane and propane and the like. However, a significant amount of steam cracking capacity operates on feedstocks which contain propane and heavier compounds. Steam cracking such feedstocks produces a hydrocarbon mixture composed of many marketable products, notably propylene, isobutylene, butadiene, amylene and pyrolytic gasoline.

Generally, in steam cracking, the cracked gases emerging from the reactors are rapidly quenched to arrest undesirable secondary reactions which destroy light olefins. Unfortunately, in addition to the foregoing desirable components, undesirable acetylenic compounds, are many times also produced. These acetylenic compounds generally are required to be removed at least to the level of a few parts per million in order for the stream to meet process requirements, for example, in polymerization processes or to avoid formation of explosive metal acetylides in equipment. Typically these acetylenic compounds are alpha-acetylenes corresponding to olefins and diolefins that were present in the steam cracking, the most common of which are vinyl acetylene, methyl acetylene and ethyl acetylene.

If allowed to remain in the hydrocarbon mixture, these acetylenic compounds may cause fouling of the equipment, interfere with polymerization reactions, and in some cases pose safety hazards. It is, therefore, highly desirable to remove these acetylenic compounds from the hydrocarbon mixture.

In hydrocarbon processing it is known that the acetylenic compounds may be removed by distillation. It is also known that the acetylenic compounds can be selectively hydrogenated and thereby removed from a hydrocarbon stream by passing a mixture of the hydrocarbon with hydrogen over a catalyst of moderate activity, for example, a copper catalyst. The location and complexity of a typical hydrogenation unit is set by the compatibility of process conditions with the catalyst system used for the selective hydrogenation of these contaminants. Typical hydrogenation units required for the production of marketable distillation products include, in addition to the acetylene converter which treats the $C_2$ stream, a methylacetylene/propadiene converter ahead of the $C_3$ splitter to remove contaminants from propylene and propane products and to avoid the risk of detonation in the $C_3$ splitter caused by build-up of methylacetylene and propadiene; a hydrogenation unit ahead of the debutanizer to remove alpha acetylenes from $C_4$ and $C_5$ olefins; a hydrogenation unit on the debutanizer overhead to remove alpha acetylenes from $C_4$ olefins; and either a heat soaker or a hydrogenation unit on the debutanizer bottoms to remove additional $C_5$ acetylenes from pyrolysis gasoline.

Generally, hydrocarbon feeds which contain the aforementioned acetylenic contaminants are introduced to a hydrogenation unit wherein they are reacted with hydrogen under conditions of temperature, pressure and over a catalyst selective for the hydrogenation of the contaminants contained therein. Catalysts suitable for use in hydrogenating acetylenic contaminants are described in U.S. Pat. Nos. 3,076,858, 3,327,013, and 4,101,451, all herein incorporated by reference.

While hydrogenation may help eliminate undesirable acetylenic compounds, other undesirable compounds are produced as by-products during hydrogenation.

Specifically, in a butadiene recovery unit, the first step is generally to hydrogenate the acetylenic contaminants in a hydrogenation unit. Side reactions in the hydrogenation unit produce other undesirable compounds that are known collectively as "green oil."

"Green oil" refers to a mixture of compounds produced in the hydrogenation of a butadiene containing hydrocarbon mixture and is known to contain oligomers of butadiene, sometimes referred to as dimers and trimers, and may contain material having up to 16 or more carbon atoms per molecule.

In conventional hydrocarbon processing methods for butadiene recovery, the butadiene and other $C_4$ hydrocarbons are generally separated from the green oil by fractional distillation in a green oil or debutanizer tower. This green oil or debutanizer tower represents a major investment item in a butadiene recovery unit in terms of its initial cost of construction, as well as its cost of maintenance and operation.

It would, therefore, be highly desirable to have a hydrocarbon processing method for butadiene recovery wherein the need for a green oil or debutanizer tower is eliminated.

SUMMARY OF THE INVENTION

This invention successfully addresses the need for a hydrocarbon processing method wherein hydrogenation by-products, known as green oil, created by the hydrogenation of a hydrocarbon stream to remove acetylenic contaminants, are separated from desirable hydrocarbons components which eliminates the need for a hydrogenation by-products distillation tower.

According to the present invention, there is provided a method of removing hydrogenation by-products which comprises the use of an extractive distillation tower operated in combination with a solvent stripper, hydrocarbon purge and a water wash column. By the arrangement of the various feeds to and between the above mentioned, the green oil may be extracted away from desirable hydrocarbons.

According to one embodiment of the present invention, the first step requires the extractive distillation of the hydrocarbon feed into an overhead stream of compounds more volatile than butadiene, and a bottoms stream of compounds of equal or lower volatility than butadiene. Next the overhead stream is fed to a first water wash tower to recover any solvent. The bottoms containing most of the solvent, green oil and butadiene, are fed to a stripper, where the butadiene is stripped overhead. A portion of the stripper bottoms is recycled to the extractive distillation tower, with the remainder portion of the stripper bottoms further processed in a second water wash tower to separate the solvent for recycle, and remove the green oil. In an optional embodiment, the remainder portion is further processed in the first water wash tower to separate the solvent for recycle and remove the green oil.

BRIEF DESCRIPTION OF THE DRAWINGS

The above and other embodiments of the present invention may be more fully understood from the following detailed description, when taken together with the accompanying drawings wherein similar reference characters refer to similar elements throughout.

DETAILED DESCRIPTION OF THE INVENTION

The present invention comprises hydrocarbon processing methods for the removal of hydrogenation by-products in the fractional distillation of light end hydrocarbon components. Specifically, in a butadiene recovery unit this invention comprises a hydrocarbon processing method which eliminates the need for the conventional hydrogenation by-products distillation tower and thereby reduces the costs of the butadiene recovery unit.

The process of the present invention for the removal of green oil from a hydrocarbon stream, will be described by reference also the conventional method for green oil removal.

Figure 1:
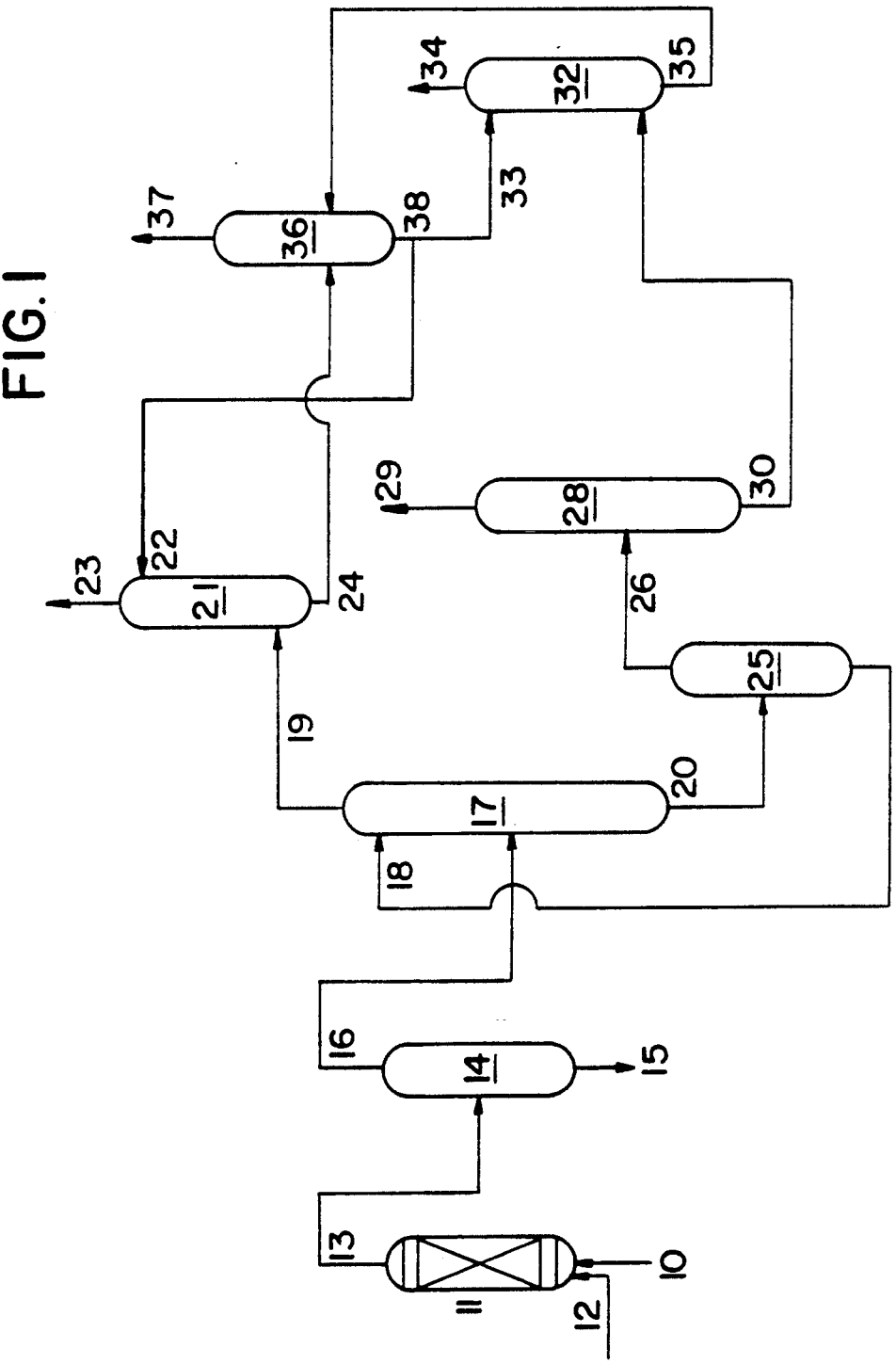
FIG. 1 is a flow diagram of a conventional butadiene recovery unit.

Referring now to the drawings, FIG. 1 is a schematic illustration of a conventional butadiene recovery unit for the separation of butadiene from a raw or crude $C_4$ hydrocarbon stream. Feedstock stream 10 comprises a raw or crude $C_4$ hydrocarbon stream which is fed to hydrogenation unit 11 wherein the raw $C_4$ hydrogenation stream 10 is reacted with hydrogen stream 12 under conditions of temperature, pressure, and over a catalyst selective for the hydrogenation of the acetylenic contaminants contained therein. Typically stream 10 is obtained from a stream cracker. The source of hydrogen stream 12 may be either from a high purity hydrogen source or from tail gas obtained from the pyrolysis effluent which contains sufficient levels of hydrogen for efficient hydrogenation to take place, thereby eliminating the expense associated with the use of a high purity hydrogen source. Although stream 10 and stream 12 are shown being fed to hydrogenation unit 11 as separate streams, it is understood that stream 10 and stream 12 may be contacted together and fed into unit 11 as one stream.

It is in hydrogenation unit 11 that the green oil is produced as a by-product of the hydrogenation of the acetylenic compounds. Hydrogenation of the $C_4$ hydrocarbon mixture generates, in addition to desirable unsaturated $C_4$ hydrocarbons, hydrogenation by-products, which by-products are referred to as green oil. This green oil includes a mixture of oligomers of butadiene, sometimes referred to as dimers and trimers, and may contain material having up to sixteen or more carbon atoms per molecule. Although there is no one component that makes up a majority of the green oil, one identified component of the green oil is 4-vinyl cyclohexene.

Following the hydrogenation, hydrogenated stream 13 leaving the hydrogenation unit 11 may contain excess hydrogen, and may optionally be treated to remove the excess hydrogen. Methods of removing excess hydrogen from hydrocarbon stream are well known, and one suitable method of removing the excess hydrogen would include the use downstream of a vent condenser to vent the excess hydrogen.

The hydrogenated stream 13, which in addition to butadiene contains a mixture of $C_4$ hydrocarbons and green oil, is fed to fractional distillation tower 14, which is also referred to as a green oil tower or a debutanizer tower. It is this distillation tower that the hydrocarbon processing method of the present invention eliminates.

Hydrogenated stream 13 is separated by distillation within the green oil tower 14 into a green oil tower overhead stream 16 and a green oil tower bottoms stream 15. Overhead stream 16 contains the desirable butadiene together with paraffinic and olefinic $C_4$ compounds, and bottoms stream 15 contains the green oil along with a portion of the $C_4$ hydrocarbons.

Bottoms stream 15, containing the green oil, may then be sent on to the distillation train of the steam cracker or returned as feed to the steam cracker.

Green oil tower overhead stream 16 is then fed to extractive distillation tower 17, wherein it is fractionated into an extractive distillation tower overhead stream 19 and an extractive distillation tower bottoms stream 20. Extractive distillation is applicable to systems in which the relative volatility of the desired component is so close to unity, relative to the other components, that separation by straight distillation is impractical. A polar organic solvent stream 18 is introduced into extractive distillation tower 17 and contacted with the $C_4$ hydrocarbon mixture in order to enhance the separation of paraffinic and olefinic $C_4$ compounds from butadiene by changing the relative volatility relationship among the components. Polar solvent stream 18 may comprise any water soluble polar organic solvent, such as acetonitrile.

Overhead stream 19 from extractive distillation tower 17 contains paraffinic and olefinic $C_4$ compounds together with a quantity of the polar solvent and is commonly referred to as raffinate 1 or butenes. Extractive distillation tower 17 may optionally employ a vent condenser in the overhead distillate drum to help remove any excess hydrogen that may be in the system from the hydrogenation unit 11.

Overhead stream 19 is fed to first water wash tower 21 wherein by contact with water supplied to the tower by stream 22 the polar organic solvent residual content of stream 19 is extracted into an aqueous phase which leaves as a first water wash bottoms stream 24 and paraffinic and olefinic $C_4$ hydrocarbon components leave as first water wash overhead stream 23.

Bottoms stream 20 from extractive distillation tower 17 contains a mixture of butadiene, residual $C_4$ components and solvent and is fed to solvent stripper 25 wherein the butadiene is stripped from the solvent and leaves as solvent stripper overhead stream 26 and the solvent leaves as solvent stripper bottoms stream 27. Butadiene stream 26 is introduced into purification tower 28, which is sometimes referred to as a tailing tower or a rerun tower. Purification tower 28 serves to improve the butadiene purity to desired levels to yield a butadiene product stream 29 and a $C_4$ hydrocarbon purge stream 30 consisting of separated hydrocarbon impurities and residual solvent and which is sent to second water wash tower 32, in order to recover the residual solvent. Water stream 33 is introduced into the second water wash tower 32 in order to effect residual solvent recovery. The clean $C_4$ hydrocarbon purge stream 34 may optionally be treated as a product stream or may be sent to a fractionator tower upstream of the butadiene production plant for recovery of its constituents.

Solvent and water mixture stream 35 from second water wash tower 32 and the solvent and water mixture stream 24 from the first water wash tower 21, are introduced into solvent purification tower 36 which separates the solvent and water feed into purified solvent stream 37 which may be recovered for recycling, and water stream 38 which may be recycled to the first and/or second water wash towers.

Figure 2:
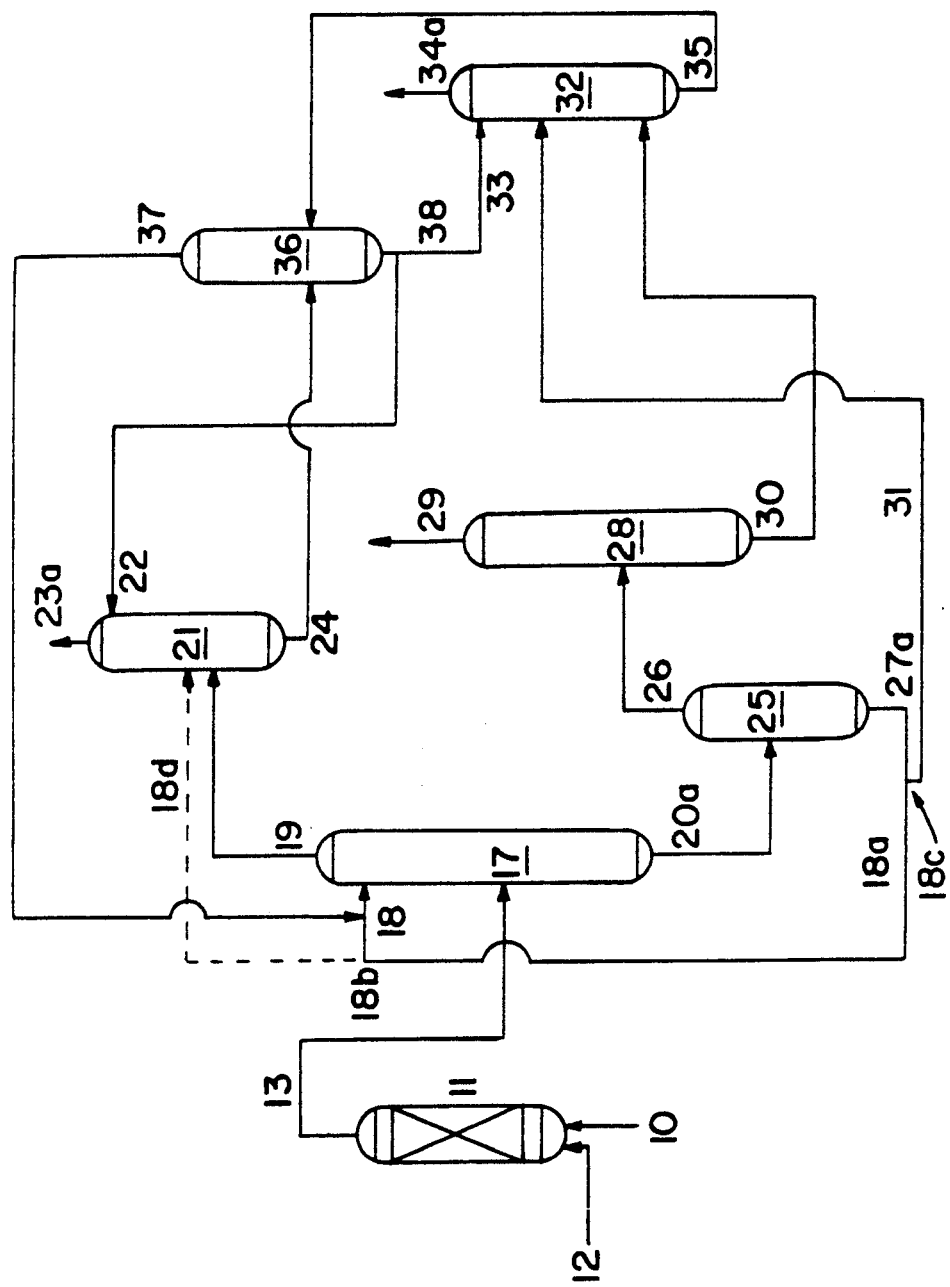
FIG. 2 is a flow diagram of a butadiene recovery unit which operates in accordance with the process of the present invention for the separation of butadiene from green oil.

Referring now to FIG. 2 and the subsequent discussion describes, without in any way limiting the scope of the present invention, particular embodiments of the present invention.

Feedstock stream 10 comprises a raw or crude $C_4$ hydrocarbon stream which is fed to a hydrogenation unit 11 wherein the $C_4$ hydrocarbon stream 10 is reacted with hydrogen stream 12 under conditions of temperature, pressure, and over a catalyst selective for the hydrogenation of the acetylenic contaminants contained therein. Typically, stream 10 is obtained from a steam cracker. Again, although stream 10 and stream 12 are shown being fed to hydrogenation unit 11 as separate streams, it is understood that stream 10 and stream 12 may be contacted together and fed into unit 11 as one stream.

The source of hydrogen stream 12 may be either from a high purity hydrogen sources or from tail gas obtained from the pyrolysis effluent which contains sufficient levels of hydrogen for efficient hydrogenation to take place, thereby eliminating the expense associated with the use of a high purity hydrogen source.

It is in hydrogenation unit 11 that the green oil is produced as a by-product of the hydrogenation the of the acetylenic compounds. Hydrogenation of the $C_4$ hydrocarbon mixture generates, in addition to desirable hydrocarbons, hydrogenation by-products, which by-products are referred to as green oil. This green oil includes a mixture of oligomers of butadiene, sometimes referred to as dimers and trimers, and may contain material having up to sixteen or more carbon atoms per molecule. Although there is generally no one component that makes up a majority of the green oil, one identified component of the green oil is 4-vinyl cyclohexene.

Following the hydrogenation, hydrogenated stream 13 leaving the hydrogenation unit 11 may contain excess hydrogen, and may optionally be treated to remove the excess hydrogen. Methods of removing excess hydrogen from hydrocarbon stream are well known, and one suitable method of removing the excess hydrogen would include the use downstream of a vent condenser to vent the excess hydrogen.

The hydrogenated stream 13, which contains in addition to butadiene, a mixture of $C_4$ hydrocarbons and green oil, is fed to extractive distillation tower 17, wherein the hydrocarbon mixture is fractionated into an overhead stream 19 comprising predominately, compounds of greater volatility than butadiene, and a bottoms stream 20a comprising predominately, compounds of equal or less volatility than butadiene.

Extractive distillation tower 17 may optionally employ a vent condenser in the overhead distillate drum to help remove any excess hydrogen that may be in the system from the hydrogenation unit 11.

A water soluble polar organic solvent stream 18 is introduced into extractive distillation tower 17 in order to enhance the separation of paraffinic and olefinic $C_4$ compounds by changing the relative volatility relationship among the components. Polar solvent stream 18 may comprise any water soluble polar organic solvent that is able to help to enhance the separation of paraffinic and olefinic $C_4$ compounds by changing the relative volatility relationship among the components. A non-limiting example of a suitable polar solvent is acetonitrile.

The overhead stream 19 contains paraffinic and olefinic $C_4$ compounds and is commonly referred to as raffinate 1 or butenes. Generally, at least 70 weight percent of the compounds of volatility greater than that of butadiene that are fed to tower 17 will be recovered in overhead stream 19. Preferably, at least 85 weight percent, and most preferably, at least 95 weight percent are recovered.

Bottoms stream 20a from extractive distillation tower 17 contains a mixture of butadiene, residual $C_4$ components, solvent and green oil. Generally, at least 70 weight percent of the butadiene and the compounds of volatility about that and less than that of butadiene that are fed to tower 17 will be recovered in bottoms stream 20a. Preferably, at least 85 weight percent, and most preferably, at least 95 weight percent are recovered.

Once it leaves extractive distillation tower 17, overhead stream 19 is fed to water wash tower 21 wherein it is contacted with water supplied to wash tower 21 by aqueous stream 22. Generally, at least 70 weight percent of the polar organic solvent residual content fed to tower 21 is extracted into an aqueous phase which leaves as a bottom stream 24. Preferably, at least 85 weight percent, and most preferably, at least 95 weight percent of the polar organic solvent residual content fed to tower 21 is extracted into an aqueous phase which leaves as bottoms stream 24. Generally, at least 70 weight percent of the paraffinic and olefinic $C_4$ hydrocarbon components fed to tower 21 leave as top stream 23a. Preferably, at least 85 weight percent, and most preferably, at least 95 weight percent of the hydrocarbon components fed to tower 21 leave as top stream 23a.

Bottoms stream 20a from extractive distillation tower 17 is fed to solvent stripper 25 wherein butadiene is separated from the solvent into which the green oil has partitioned in the extractive distillation tower 17.

Once the butadiene is separated from the solvent in tower 25, it leaves tower 25 as overhead stream 26. Generally, at least 70 weight percent of the butadiene from feed stream 20a is recovered in overhead stream 26. Preferably, at least 85 weight percent, and most preferably, at least 95 weight percent of the butadiene from feed stream 20a is recovered in overhead stream 26.

Optionally, the purity of the butadiene recovered from tower 25 may be enhanced by further distillation in butadiene purification tower 28. Butadiene stream 26 is introduced into purification tower 28 which is sometimes referred to as a tailing tower or a rerun tower. Purification tower 28 serves to improve the butadiene purity to desired levels to yield a butadiene product stream 29 and a $C_4$ hydrocarbon purge stream 30 consisting of separated hydrocarbon impurities and residual solvent which is sent to a $C_4$ hydrocarbon purge water wash tower 32 in order to recover additional residual solvent.

The solvent containing green oil in tower 25 leaves as a liquid phase bottoms stream 27a. Generally, at least 70 weight percent of the solvent containing green oil from feed stream 20a is recovered in bottoms stream 27a. Preferably, at least 85 weight percent, and most preferably, at least 95 weight percent of the solvent containing green oil from feed stream 20a is recovered in bottoms stream 27a.

At least a portion of the green oil containing solvent which leaves stripper 25 as bottoms stream 27a may be recirculated by stream 18a into the solvent feed stream 18 to extractive distillation tower 17. The amount of green oil recirculating in the system is controlled by purge streams 18d or 31. The remaining portion of the green oil containing solvent is treated for removal of green oil by liquid/liquid extraction in either water wash tower 21 and/or water wash tower 32 to provide recovered solvent for recycle. The purge streams 18d or 31 may optionally be fed to an intermediary stage between the water and hydrocarbon feeds on water wash towers 21 and 32, respectively.

One of two alternative procedures may be utilized to remove green oil from the remaining solvent portion. In one the entire quantity of green oil containing solvent leaving solvent stripper 25 as bottoms 27a may be conveyed in line 18a to a split point 18b wherein it is split into two portions, one of which is supplied to line 18 into tower 17 and the second portion being conveyed by line 18d to water wash tower 21. Alternatively, the green oil containing solvent bottoms from stripper 25 may be split at point 18c the first portion being routed by line 18a to line 18 and into tower 17 and the second portion being conveyed by line 31 to a $C_4$ hydrocarbon purge water wash tower 32.

With regard to the first alternative, that of routing a portion of green oil-solvent to water wash tower 21, this embodiment is preferred in those circumstances wherein green oil contamination of the hydrocarbons in the overhead stream 23a from tower 21 is of no concern. In this circumstance, the flow rate of olefinic and paraffinic hydrocarbons by line 19 and of water by aqueous stream 22 to tower 21 is more than sufficient to ensure the maintenance of two liquid phases, one organic and the other aqueous, within tower 21 which is adequate to cause extraction of the green oil into the organic phase which leaves tower 21 as a top stream 23a while solvent partitions into the aqueous phase which leaves tower 21 as bottoms stream 24. The aqueous solvent stream 24 is introduced to solvent purification tower 36 wherein solvent 37 is recovered for reuse from water stream 38 which is returned to the water wash towers.

Wherein the overhead stream of tower 21 is intended to be utilized in processes that are sensitive to green oil contamination, it is desirable to avoid its contamination with green oil, and therefore, stream 18d should not be utilized. In this circumstance it is preferred to split the green oil containing solvent bottoms from stripper 25 at split point 18c, and by line 31 route that portion to be treated for green oil removal to the $C_4$ hydrocarbon purge water wash tower 32. The quantity of $C_4$ hydrocarbons in the solvent purge of line 31 and in line 30 may be inadequate to ensure the maintenance of an organic liquid phase together with a liquid water phase in tower 32 which will cause extraction of the green contaminant oil into an organic liquid phase, which leaves tower 32 as contaminant containing stream 34a, while solvent partitions into the aqueous phase which leaves tower 32 as solvent and water mixture stream 35. Accordingly, when this embodiment is utilized liquified quantity of hydrocarbons will generally be added to tower 32 which is in addition to that quantity which is contained in line 30 and as a residual amount in the solvent feed 31 to the tower. This is readily accomplished by routing a stream containing $C_4$ hydrocarbons, for example a portion of the $C_4$ containing hydrocarbon stream 10, to a point near or preferably at the bottom of tower 32.

Solvent and water mixture stream 35 along with solvent and water mixture stream 24 are introduced into solvent purification tower 36 wherein solvent stream 37 is recovered for recycle to tower 17, and water stream 38 is recycled to water wash tower 21 or water wash tower 32.

Any stream containing hydrocarbons could be utilized as the liquefied quantity of hydrocarbons described above as long as the percentage green oil content of such a stream is sufficiently low. Preferably, the stream will comprise $C_4$ or $C_5$ hydrocarbons. The percentage green oil content of such a stream will be less than that of solvent purge line 31 or residual solvent stream 30. Preferably, the green oil content is sufficiently low so that the water recovered from solvent and water stream 35, ultimately recovered water stream 38, could be recycled to either water wash 21 or water wash 32 without undue detrimental effects on the process. This generally means that solvent and water stream 35 will comprise no more than about 0.1 weight percent green oil, preferably no more than about 0.01 weight percent green oil, and most preferably no more than about 0.001 weight percent green oil.

In the second embodiment it is preferred to supply the green oil containing solvent to the water wash tower at a point which is intermediate between the water supply stream 33 and the hydrocarbon stream feed point from stream 10 located at or near the bottom of tower 32.

Within these water wash towers the green oil will preferentially partition into the liquid organic phase therein, either the contaminant containing hydrocarbon stream 24a or 34a, depending on which of the two alternatives is chosen. Depending on process conditions, either the water or the hydrocarbon phase may be the dispersed phase.

It is preferred to maintain the amount of green oil in that total amount of solvent supplied as feed to extractive distillation tower 17 to a total of less than about 10 wt %, preferably less than about 3 wt % and most preferably less than about 1.6 wt %. Accordingly, in comparison to conventional process designs for a butadiene recovery unit wherein green oil is removed by fractional distillation before the butadiene containing stream is fed to an extractive distillation tower, wherein a solvent purge circulation rate of about only 1% is typical, in the process of this invention a solvent purge circulation rate of from about 1 percent to about 10 percent, preferably about 3 to about 7 percent, and most preferably about 4 percent to about 6 percent is employed. As a further advantage of the increased solvent purge circulation rate it has been determined that the amount of decomposed solvent by-products such as acetamide, acetic acid, ammonia, etc. present in the solvent supplied to tower 17 is reduced, compared to that of conventional units, which beneficially decreases the occurrence and amount of foaming in tower 17. The ratio of water to solvent needed to purge green oil from the solvent in either of the water wash towers 21 or 32 ranges in a weight ratio, water to solvent, of from about 0.5 to about 4, and preferably from about 1 to about 3. As noted, when the green oil purge is accomplished in tower 21 there is no need to supply a supplemental hydrocarbon feed to this tower. In the other embodiment wherein green oil purge is accomplished in tower 32, a feed of supplemental hydrocarbons in a weight ratio to that content of hydrocarbons supplied by line 30 to tower 32 may range from about 0 to about 100, preferably from about 0.1 to about 2 and more preferably from about 0.9 to about 1.6. The water wash tower, whether tower 21 or 32, is maintained at an operating temperature of from about 60° to about 150° F. and preferably at about 100° F.

In a conventional plant, as described above, there would be a hydrogenation by-product or green oil distillation tower which would remove the green oil from the hydrogenation reactor product. As shown above, the present invention obviates the need for such a tower. A further benefit is that the liquid-liquid extraction method used in the present invention is more energy efficient than separating green oil from butadiene by distillation.

While the present invention has been described in terms of a butadiene recovery unit which recoveries butadiene from a stream containing butadiene and contaminant oligomers of butadiene, such as dimers and trimers of butadiene, the present invention has universal applicability to recovering a specific diolefin from a stream containing the desired diolefin and contaminant oligomers of that diolefin such as dimers and trimers of that diolefin.

From this description of preferred embodiments of the invention, those skilled in the art may find variations and adaptations thereof, and all such variations and adaptations, falling within the scope and spirit of this invention, are intended to be covered by the claims which follow.

We claim:

1. A process for recovering butadiene from a hydrocarbon stream comprising, butadiene, other hydrocarbon components having volatilities in the range of lower to higher than the volatility of butadiene, and contaminants, wherein the contaminants comprise oligomers of butadiene, the process comprising:
    (a) contacting the hydrocarbon stream with a water soluble polar solvent;
    (b) separating the contacted product of step (a) into a light stream and a solvent stream, wherein the light stream comprises at least 70 weight percent of the other hydrocarbon components of the hydrocarbon stream having a higher volatility than butadiene, and the solvent stream comprises at least 70 weight percent of: the butadiene, solvent, contaminants, and other hydrocarbon components of the hydrocarbon stream having a volatility about that of butadiene or lower;
    (c) separating the solvent stream of step (b) into a butadiene stream and a stripped solvent stream, wherein the butadiene stream comprises at least 70 weight percent of: the butadiene of the solvent stream and other hydrocarbon components of the solvent stream, and the stripped solvent steam comprises at least 70 weight percent of: the solvent of the solvent stream and the contaminants of the solvent stream;
    (d) recycling at least a portion of the stripped solvent stream of step (c) to step (a) wherein it comprises at least a portion of the solvent in step (a);
    (e) contacting in a first water wash step, the light stream and the stripped solvent stream of step (c) not recycled in step (d), with an aqueous solution to form a solvent and water phase and a contaminant containing hydrocarbon phase; and
    (f) recovering a solvent and water stream and a contaminant containing hydrocarbon stream from the first water wash of step (e).

2. The process of claim 1 wherein the first water wash utilizes at least one contacting device selected from the group consisting of trays and packing.

3. The process of claim 1 wherein the polar solvent comprises acetonitrile.

4. The process of claim 1 further comprising the step of:
    separating the solvent and water stream into a recovered solvent stream and a recovered water stream.

5. The process of claim 4 further comprising the step of:
    recycling the recovered water stream to step (e).

6. The process of claim 4 further comprising the step of:
    recycling the recovered solvent stream to step (a).

7. The process of claim 1 further comprising the step of:
    separating the butadiene stream of step (c) into a purified butadiene stream and a residual solvent stream, wherein the purified butadiene stream has a greater butadiene fraction than the butadiene stream of step (c).

8. The process of claim 7 further comprising the steps of:
    contacting in a second water wash step, the residual solvent stream with an aqueous solution to form a solvent and water phase and a contaminant containing hydrocarbon phase; and
    recovering a solvent and water stream and a contaminant containing hydrocarbon stream from the contacted product of the second water wash step.

9. The process of claim 8 wherein the second water wash step utilizes at least one contacting device selected from the group consisting of trays and packing.

10. The process of claim 8 further comprising the step of:

separating the solvent and water stream of into a solvent stream and a water stream.

11. The process of claim 10 further comprising the step of:

recycling the water stream to the contacting step.

12. The process of claim 10 further comprising the step of:

recycling the solvent stream to step (a).

13. A process for recovering butadiene from a hydrocarbon stream comprising butadiene, contaminants and other hydrocarbon components, wherein the contaminants comprise oligomers of butadiene, the process comprising:

(a) contacting the hydrocarbon stream with a water soluble polar solvent;

(b) separating the contacted product of step (a) into a light stream and a solvent stream, wherein the light stream comprises at least 70 weight percent of the other hydrocarbon components of the hydrocarbon stream of higher volatility than butadiene, and the solvent stream comprises at least 70 weight percent of: the butadiene, solvent, contaminants, and other hydrocarbon components of the hydrocarbon stream having an volatility about that of butadiene or lower;

(c) separating the solvent stream of step (b) into a butadiene stream and a stripped solvent stream, wherein the butadiene stream comprises at least 70 weight percent of: the butadiene of the solvent stream and other hydrocarbon components of the solvent stream, and the stripped solvent stream comprises at least 70 weight percent of: the solvent of the solvent stream and the contaminants of the solvent stream;

(d) separating the butadiene stream of step (c) into a purified butadiene stream and a residual solvent stream, wherein the purified butadiene stream has a greater butadiene fraction than the butadiene stream of step (c);

(e) recycling at least a portion of the stripped solvent stream to step (a);

(f) contacting in a first water wash step, the light stream with an aqueous solution to form a solvent and water phase and a contaminant containing hydrocarbon phase;

(g) contacting in a second water wash step, the stripped solvent stream of step (c) not recycled in step (e), the residual solvent stream and an aqueous stream; and (h) recovering a solvent and water stream and a contaminant containing hydrocarbon stream from the first water wash, and a solvent and water stream and a hydrocarbon stream from the second water wash.

14. The process of claim 13 further comprising the step of:

separating each solvent and water stream into a recovered solvent stream and a recovered water stream.

15. The process of claim 14 wherein the first and second water wash steps utilize at least one contacting device selected from the group consisting of trays and packing.

16. The process of claim 14 wherein step (g) further comprises contacting in the second wash step the stripped solvent stream not recycled in step (e), the residual solvent stream, an aqueous stream, and a supplemental hydrocarbon stream comprising $C_4$ or $C_5$ hydrocarbons and to form an aqueous phase and a hydrocarbon phase wherein the supplemental stream has a contaminant content less than about 0.1 weight percent of the stream.

17. The process of claim 14 further comprising the step of:

recycling the recovered water stream to the first water wash and the second water wash.

18. The process of claim 17 wherein step (g) further comprises contacting in the second wash step the stripped solvent stream of step (c) not recycled in step (e), the residual solvent stream, an aqueous stream, and a supplemental hydrocarbon stream comprising $C_4$ or $C_5$ hydrocarbons to form an aqueous phase and a hydrocarbon phase and wherein the supplemental stream has a contaminant content less than about 0.1 weight percent of the stream.

19. The process of claim 18 further comprising the step of:

recycling the recovered solvent stream of to step (a).

20. A process for recovering a diolefin from a hydrocarbon stream comprising, the diolefin, other hydrocarbon components having volatiles in the range of lower to higher than the volatility of the diolefin, and contaminants, wherein the contaminants comprise oligomers of the diolefin, the process comprising:

(a) contacting the hydrocarbon stream with a water soluble polar solvent;

(b) separating the contacted product of step (a) into a light stream and a solvent stream, wherein the light stream comprises at least 70 weight percent of the other hydrocarbon components of the hydrocarbon stream of having a higher volatility than the diolefin, and the solvent stream comprises at least 70 weight percent of: the diolefin, solvent, contaminants, and other hydrocarbon components of the hydrocarbon stream having an volatility about that of the diolefin or lower;

(c) separating the solvent stream of step (b) into a diolefin stream and a stripped solvent stream, wherein the diolefin stream comprises at least 70 weight percent of: the diolefin of the solvent stream and other hydrocarbon components of the solvent stream, and the stripped solvent stream comprises at least 70 weight percent of: the solvent of the solvent stream and the contaminants of the solvent stream;

(d) recycling at least a portion of the stripped solvent stream to step (a);

(e) contacting in a first water wash step, the light stream and the stripped solvent stream not recycled in step (d) with an aqueous solution to form a solvent and water phase and a contaminant containing hydrocarbon phase; and (f) recovering a solvent and water stream and a contaminant containing hydrocarbon stream from the first water wash.

21. A process for recovering a diolefin from a hydrocarbon stream comprising the diolefin, contaminants, and other hydrocarbon components, wherein the contaminants comprise oligomers of the diolefin, the process comprising:

(a) contacting the hydrocarbon stream with a water soluble polar solvent;

(b) separating the contacted product of step (a) into a light stream and a solvent stream, wherein the light stream comprises at least 70 weight percent of the other hydrocarbon components of the hydrocarbon stream of higher volatility than the diolefin, and the solvent stream comprises at least 70 weight percent of: the diolefin, solvent, contaminants, and other hydrocarbon components of the hydrocarbon stream having an volatility about that of the diolefin or lower;

(c) separating the solvent stream of step (b) into a diolefin stream and a stripped solvent stream, wherein the diolefin stream comprises at least 70 weight percent of: the diolefin of the solvent stream and other hydrocarbon components of the solvent stream, and the stripped solvent stream comprises at least 70 weight percent of: the solvent of the solvent stream and the contaminants of the solvent stream;

(d) separating the diolefin stream of into a purified diolefin stream and a residual solvent stream, wherein the purified diolefin stream has a greater diolefin fraction than the diolefin stream of step (c);

(e) recycling at least a portion of the stripped solvent stream to step (a);

(f) contacting in a first water wash step, the light stream with an aqueous solution to form a solvent and water phase and a contaminant containing hydrocarbon stream;

(g) contacting in a second water wash step, the stripped solvent stream not recycled in step (e), the residual solvent stream and an aqueous stream to form a solvent and water phase and a contaminant containing hydrocarbon stream; and (h) recovering a solvent and water stream and a contaminant containing hydrocarbon stream from the first water wash, and a solvent and water stream and a contaminant containing hydrocarbon stream from the second water wash.

22. The process of claim 21 wherein step (g) further comprises contacting in the second wash step the stripped solvent stream not recycled in step (e), the residual solvent stream, an aqueous stream, and a supplemental hydrocarbon stream comprising $C_4$ or $C_5$ hydrocarbons to form an aqueous phase and a hydrocarbon phase and wherein the supplemental stream has a contaminant content less than about 0.1 weight percent of the stream.

* * * * *